United States Patent [19]
Crane et al.

[11] Patent Number: 5,973,193
[45] Date of Patent: Oct. 26, 1999

[54] ETHYL ACETATE SYNTHESIS FROM ETHYLENE AND ACETIC ACID USING SOLID ACID CATALYSTS

[75] Inventors: Robert A. Crane, Monroeville; Stephen H. Brown, Princeton, both of N.J.; Lorenzo De Caul, Wilmington, Del.

[73] Assignee: Mobil Oil Corporation, Fairfax, Va.

[21] Appl. No.: 09/116,385

[22] Filed: Jul. 16, 1998

[51] Int. Cl.$^6$ ................................................ C07C 67/04
[52] U.S. Cl. ............................................................ 560/247
[58] Field of Search ............................................. 560/247

[56] References Cited

U.S. PATENT DOCUMENTS 4,365,084  12/1982  Young ........................................ 560/247
4,448,983   5/1984  Young ........................................ 560/241.1
5,225,388   7/1993  Wunder et al. ........................... 502/170

FOREIGN PATENT DOCUMENTS 0 031 252  7/1981  European Pat. Off. .
0 073 141  3/1983  European Pat. Off. .
0 538 826  4/1993  European Pat. Off. .

*Primary Examiner*—Gary Geist
*Assistant Examiner*—Robert W. Deemie
*Attorney, Agent, or Firm*—Penny L. Prater; Malcolm D. Keen

[57] ABSTRACT

A method of producing ethyl acetate by reacting acetic acid with ethylene in the presence of a solid acidic catalyst comprising a zeolite selected from the group consisting of MCM-22, MCM-49, MCM-56, ZSM-5 and zeolite-Beta.

7 Claims, No Drawings

ETHYL ACETATE SYNTHESIS FROM ETHYLENE AND ACETIC ACID USING SOLID ACID CATALYSTS

FIELD OF THE INVENTION

The present invention is directed to a method of reacting acetic acid directly with ethylene, so as to form ethyl acetate without a water by-product.

BACKGROUND OF THE INVENTION

Ethyl acetate is useful in coating materials, as a solvent and as a starting material for a number of important industrial processes.

Conventionally, the formation of ethyl acetate was by esterification of acetic acid with ethanol, using an acidic catalyst, such as a mineral acid:

(1) $CH_3OOH + C_2H_5OH \rightarrow CH_3COOC_2H_5 + H_2O$; or by direct synthesis from acetaldehyde:

(2) $2CH_3CHO \rightarrow CH_3COOC_2H_5$.

However, since the esterification reaction (1) is an equilibrium reaction, it is necessary to continuously remove the water by-product in order to achieve high conversion efficiencies to ethyl acetate. Unfortunately, most known methods of water removal, such as distillation, are either energy intensive, expensive, or both. An additional drawback to reaction pathway (1) is that ethanol is a relatively expensive feedstock. Likewise, reaction (2) is unfavorable, since the starting material itself, acetaldehyde, is relatively expensive and quite unstable.

Accordingly, it would be optimum to be able to form ethyl acetate with relatively low value reactants and without the formation of water by-product to reduce the energy required to separate the water by-product from the ethyl acetate product. Formation of ethyl acetate by reacting acetic acid with ethylene solves both the stated problems. Ethylene is a low value olefinic gas produced in large quantities in many petroleum refineries, which if useful as a reactant in place of ethanol, would result in a direct cost savings with respect to the reactant feed. Also, since water would not be produced as a by-product, it would not be necessary to incur the expense of separating water from the desired product, ethyl acetate, such as by the energy intensive distillation process.

Several investigators have developed processes suitable for direct reaction of ethylene with acetic acid to form ethyl acetate. EP 0 031 252 A1 discloses proton-catalyzed reactions in which water is not a stoichiometric reactant catalyzed by metal cation-exchanged layered clays. Reaction of ethylene with acetic acid is disclosed. EP 0 073 141 A2 discloses a method for promoting the activity and/or extending the life of a cation-exchangeable layered clay catalyst, for example montmorillonite, bentonite or vermiculite, which catalysts are useful in the formation of esters from olefins and carboxylic acids. Reaction of ethylene with acetic acid to form ethyl acetate is disclosed. EP 0 538 826 A2 discloses reacting ethylene with acetic acid in the presence of a tungstophosphoric acid catalyst having a portion of the acidic protons of the tungstophosphoric acid replaced with cesium cations.

U.S. Pat. No. 4,365,084 and U.S. Pat. No. 4,448,983 both disclose preparation of alkyl carboxylates by reaction of an olefin with a carboxylic acid in the presence of particular zeolite catalysts. Reaction of ethylene with acetic acid over HZSM-12 is disclosed (Example 16). However, the reaction level is disclosed to be low.

SUMMARY OF THE INVENTION

A first object of the present invention to develop a novel method of forming ethyl acetate, while avoiding the formation of water during the reaction.

A second object of the invention is to reduce the overall cost of producing ethyl acetate.

The present inventors have achieved the above object by developing a method of producing ethyl acetate by reacting acetic acid with ethylene in the presence of a solid acidic catalyst selected from MCM-22, MCM-49, MCM-56, ZSM-5 and zeolite-Beta.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

According to the present invention, ethyl acetate is produced by reacting acetic acid with ethylene in the presence of a solid acidic catalyst, especially a zeolite selected from MCM-22, catalysts in the MCM-22 "family", i.e. MCM-22, MCM-49 and MCM-56, ZSM-5 or zeolite-Beta. The following U.S. patents disclose the zeolites useful in this invention and are incorporated herein by reference: U.S. Pat. No. 4,954,325 (MCM-22); U.S. Pat. No. 5,236,575 (MCM-49); U.S. Pat. No. 5,326,697 (MCM-56); U.S. Pat. No. 3,702,886 (ZSM-5) and U.S. Pat. No. 3,308,069 (zeolite Beta). The MCM-22 "family" of crystalline inorganic oxide materials are generally characterized by X-ray diffraction patterns including d-spacing maxima at 12.4±0.25, 6.9±0.15, 3.57±0.07 and 3.42±0.07 Angstroms.

The zeolite catalysts according to the present invention may be used alone or in combination with other materials. In particular, the zeolites suitable for catalyzing the reaction between acetic acid and ethylene may be supported on a conventional catalyst support, such as $Al_2O_3$, or bound with conventional binders, including silica, alumina, amorphous silica-alumina or zeolite (e.g. a self-bound zeolite).

The reaction according to the present invention may be conducted in either a batch-type reaction or in a continuous-type reaction. When conducting a batch-type reaction, the mole ratio of acetic acid to ethylene charged to the reactor may vary from about 0.1 to about 10, preferably from about 0.5 to about 2. When conducting a continuous-type reaction, the weight hourly space velocity (WHSV) of acetic acid may be varied from about 0.1 to about 10, preferably from about 0.5 to about 2.

Suitable reaction temperatures may vary from about 50° C. to about 300° C., preferably about 200° C. to about 250° C. Reaction pressures may range from 50 psig (450 kPa) to about 3000 psig (21,000 kPa), preferably from about 300 psig (2200 kPa) to about 1500 psig (11,000 kPa).

In the following examples, the yield of ethyl acetate was calculated according to the following equation:

Yield=g ethyl acetate/(g ethyl acetate+g acetic acid)×100%.

EXAMPLE 1

An autoclave was loaded with acetic acid and ethylene in a weight ratio of 9:1, in the presence of MCM-22/$Al_2O_3$ catalyst. The weight ratio of total reactants to catalyst was about 10:1. The closed reactor was heated to 200° C. for 4 hours. Ethyl acetate was the only product observed. Ethyl acetate yield was 5.4 wt %.

EXAMPLE 2

An autoclave was loaded with acetic acid and ethylene in a weight ratio of about 8:1.5 in the presence of MCM-22/$Al_2O_3$ catalyst. The weight ratio of total reactants to catalyst was about 9:1. The closed reactor was heated to 200° C. for 4 hours. Ethyl acetate was the only product observed. Ethyl acetate yield was 4.2 wt %.

EXAMPLE 3

An autoclave was loaded with acetic acid and ethylene in a weight ratio of about 1:1 in the presence of MCM-22/$Al_2O_3$ catalyst. The weight ratio of total reactants to catalyst was about 13:1. The closed reactor was heated to 200° C. for 4 hours. Ethyl acetate was formed as the major product. Ethyl acetate yield was 13.9 wt %.

EXAMPLE 4

An autoclave was loaded with acetic acid and ethylene in a weight ratio of about 1:2 in the presence of MCM-22/$Al_2O_3$ catalyst. The weight ratio of total reactants to catalyst was about 10:1. The closed reactor was heated to 200° C. for 4 hours. Ethyl acetate was formed as the major product. Ethyl acetate yield was 24.5 wt %.

EXAMPLE 5

An autoclave was loaded with acetic acid and ethylene in a weight ratio of about 1:1 in the presence of MCM-22/$Al_2O_3$ catalyst, and with about 10 wt %, relative to acetic acid, of the following inert tracers: Cyclohexane and n-octane. The weight ratio of total reactants to catalyst was about 15:1. The closed reactor was heated to 200° C. for 8 hours. Ethyl acetate was formed as the major product. Ethyl acetate yield was 28.9 wt %.

EXAMPLE 6

An autoclave was loaded with acetic acid and ethylene in a weight ratio of about 1:1 in the presence of zeolite Beta catalyst, and with about 10 wt %, relative to acetic acid, of the following inert tracers: Cyclohexane and n-octane. The weight ratio of total reactants to catalyst was about 15:1. The closed reactor was heated to 200° C. for 8 hours. Ethyl acetate was formed as the major product. Ethyl acetate yield was 28.2 wt %.

EXAMPLE 7

An autoclave was loaded with acetic acid and ethylene in a weight ratio of about 1:1 in the presence of ZSM-5 catalyst, and with about 10 wt %, relative to acetic acid, of the following inert tracers: Cyclohexane and n-octane. The weight ratio of total reactants to catalyst was about 15:1. The closed reactor was heated to 200° C. for 8 hours. Ethyl acetate was formed as the major product. Ethyl acetate yield was 19.6 wt %.

EXAMPLE 8

A flow reactor was loaded with MCM-22/$Al_2O_3$ catalyst. The run conditions were: 1 WRSV acetic acid, 1:2 (molar) acetic acid:ethylene, 300 psig and 250° C. After 3 hours on stream, ethyl acetate yield was 22.1 wt %.

Comparative Example 1

An autoclave was loaded with acetic acid and ethylene in a weight ratio of about 1:1 in the presence of mordenite catalyst, and with about 10 wt %, relative to acetic acid, of the following inert tracers: Cyclohexane and n-octane. The weight ratio of total reactants to catalyst was about 15:1. The closed reactor was heated to 200° C. for 24 hours. Ethyl acetate was formed as the major product. Ethyl acetate yield was 11.0 wt %.

Comparative Example 2

An autoclave was loaded with acetic acid and ethylene in a weight ratio of about 1:1 in the presence of ZSM-12 catalyst, and with about 10 wt %, relative to acetic acid, of the following inert tracers: Cyclohexane and n-octane. The weight ratio of total reactants to catalyst was about 15:1. The closed reactor was heated to 200° C. for 24 hours. Ethyl acetate was formed as the major product. Ethyl acetate yield was 2.8 wt %.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method of producing ethyl acetate, comprising reacting acetic acid with ethylene in the presence of a solid acidic catalyst comprising a zeolite selected from the group consisting of MCM-22, MCM-49, MCM-56, ZSM-5 and zeolite-Beta.

2. A method of producing ethyl acetate, comprising reacting acetic acid with ethylene in the presence of a solid acidic catalyst comprising the zeolite MCM-22.

3. A method of producing ethyl acetate, comprising reacting acetic acid with ethylene in the presence of a solid acidic catalyst comprising zeolite-beta.

4. The method according to claim 1, wherein the mole ratio of acetic acid to ethylene ranges from about 0.1 to about 10.

5. A method of producing ethyl acetate, comprising reacting acetic acid with ethylene in the presence of a solid acidic catalyst comprising the zeolite MCM-49.

6. A method of producing ethyl acetate, comprising reacting acetic acid with ethylene in the presence of a solid acidic catalyst comprising the zeo-lite MCM-56.

7. A method of producing ethyl acetate, comprising reacting acetic acid with ethylene in the presence of a solid acidic catalyst comprising a crystalline inorganic oxide material having an X-ray diffraction pattern including d-spacing maxima at 12.4±0.25, 6.9±0.15, 3.57±0.07 and 3.42±0.07 Angstroms.

* * * * *